US008563494B2

(12) United States Patent
Wis-Surel et al.

(10) Patent No.: US 8,563,494 B2
(45) Date of Patent: Oct. 22, 2013

(54) IRIDESCENT SOAP BARS CONTAINING ETHOXYLATED ALCOHOLS

(75) Inventors: Gabriela Wis-Surel, Cos Cob, CT (US); Teanoosh Moaddel, Watertown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 1086 days.

(21) Appl. No.: 11/899,045

(22) Filed: Sep. 4, 2007

(65) Prior Publication Data

US 2009/0062169 A1 Mar. 5, 2009

(51) Int. Cl.
*A61K 8/00* (2006.01)

(52) U.S. Cl.
USPC ............ 510/141; 510/146; 510/151; 510/152

(58) Field of Classification Search
None
See application file for complete search history.

(56) References Cited

U.S. PATENT DOCUMENTS

| | | | | |
|---|---|---|---|---|
| 3,789,011 | A | 1/1974 | Tanaka | |
| 3,969,433 | A | 7/1976 | Kose et al. | |
| 5,501,812 | A * | 3/1996 | Vermeer et al. | 510/153 |
| 6,482,782 | B1 | 11/2002 | Kim | |
| 6,946,124 | B2 | 9/2005 | Arnaud-Sebillotte et al. | |
| 2003/0021817 | A1 | 1/2003 | Arnaud-Sebillotte et al. | |
| 2003/0053979 | A1 | 3/2003 | Arnaud-Sebillotte et al. | |
| 2004/0105831 | A1 | 6/2004 | Frantz et al. | |
| 2005/0158270 | A1 | 7/2005 | Frantz et al. | |

FOREIGN PATENT DOCUMENTS

| | | | |
|---|---|---|---|
| CA | 1 021 658 | A | 11/1977 |
| EP | 0 287 300 | A | 10/1988 |
| EP | 0 311 343 | A | 4/1989 |
| JP | 56 071021 | | 6/1981 |
| JP | 57 067510 | | 4/1982 |
| JP | 57 067511 | | 4/1982 |
| JP | 10 182343 | | 7/1998 |
| WO | 91/09106 | | 6/1991 |
| WO | 93/17088 | A | 9/1993 |
| WO | 95/03392 | | 2/1995 |

OTHER PUBLICATIONS

Rieger, "The Phenomena of Iridescence and Its Application", Mearl Corp., soap/cosmetics/chemical specialties for Jun. 1980, pp. 57-58, 70, 72.
Satoh, et al., "Iridescent Solutions Resulting from Periodic Structure of Bllayer Membranes", J. Phys. Chem. 1987, 91, 6629-6632.
Strey, et al., "Freeze Fracture Electron Microscopy of Dilute Lamellar and Anomalous Isotropic (L3) Phases", Langmuir, vol. 6, pp. 1635-1639 (1990).
Revol, et al., "Solid Self-Assembled Films of Cellulose with Chiral Nematic Order and Optically Variable Properties", Journal of Pulp and Paper Science: vol. 24, No. 5, May 1998, pp. 146-149.
Vukusic, et al., "Photonic structures in biology", Nature, vol. 424, Aug. 14, 2003, pp. 852-855.
International Search Report, PCT/EP2008/060322, mailed Dec. 8, 2008, 3 pp.

* cited by examiner

*Primary Examiner* — Necholus Ogden, Jr.
(74) *Attorney, Agent, or Firm* — Alan A. Bornstein

(57) ABSTRACT

An iridescent continuous phase soap bar with an ordered layered microstructure containing soap, water and specific ethoxylated alcohols is described. The phenomena of continuous phase iridescence in a soap bar is characterized as blue hue which intensity depends on the viewing angle and on the background color used for its observation by the user. In a preferred embodiment, the iridescent soap bar is prepared with mixing equipment capable of creating intensive mass shearing conditions and which generate high compression and extensional forces on the processed soap mass.

13 Claims, 7 Drawing Sheets

IRIDESCENT SOAP BARS CONTAINING ETHOXYLATED ALCOHOLS

BACKGROUND OF THE INVENTION

1. Field of the Invention

The present invention relates to a toilet bar suitable for cleansing. In particular, it relates to a toilet bar which has an ordered, layered (or multilayered) microstructure and whose continuous phase is iridescent and contains specific ethoxylated alcohols.

2. The Related Art

Iridescent, opalescent or pearly solid and liquid cosmetic products are known in the cosmetic industry and are designed to appear attractive to consumers. Iridescent, opalescent or pearly product descriptions are often used interchangeably and generally convey the fact that iridescence is a characteristic of the product. Iridescence is defined as an optical phenomenon whereby light is scattered between two ordered layers. The resulting colors and their intensity are seen to vary as a function of detection angle or observer position with respect to the article. Iridescence in a given product can arise from the continuous phase, from the dispersed phase such as from iridescent pigments or discrete particles blended into the product, or from some combination thereof.

U.S. Pat. No. 6,946,124 issued to Arnaud-Sebillotte et al. on Sep. 20, 2005 discloses an iridescent cosmetic composition that contains surfactant(s) and polymer particles in a specific diameter range. U.S. Patent Publication Nos. 2003/0021817 and 2003/0053979 both to Arnaud-Sebillotte et al. and published on Jan. 30, 2003 and Mar. 20, 2003 respectively, disclose other iridescent cosmetic compositions that contain polymer particles in a specific diameter range.

PCT publication no. WO 91/09106 to El-Nokaly et al. published on Jun. 27, 1991 discloses extruded toilet bars made with polymeric lyotropic liquid crystals that confer iridescent properties to the bars.

PCT publication no. WO 95/03392 to Dumas et al. published on Feb. 2, 1995 discloses the use of work energy of mixing to render specific soap bars transparent.

Strey at al. "Freeze Fracture Electron Microscopy of Dilute Lamellar and Anomalous Isotropic (L3) Phases", Langmuir, Vol. 6, pp. 1635-1639 (1990); discloses an investigation of a binary water-ethoxylated alcohol (EA) C12E5 system for forming a lamellar phase.

U.S. Pat. No. 3,789,011 to Tanaka, issued on Jan. 29, 1974 discloses a non-extruded melt cast transparent soap bar having pearlescent qualities that are provided by a dispersed phase composed of various inorganic materials or pigments.

U.S. Pat. No. 6,482,782 to Kim, issued on Nov. 19, 2002 also discloses a pearlescent non-extruded, melt cast soap bar containing in its dispersed phase coated micaceous powder.

Surprisingly, it was discovered that specific ethoxylated alcohols could produce iridescent continuous phase soap bars within specific formulation constraints and within a wide process window provided an ordered layered structure was present. Such process conditions are preferably characterized by 1) selective binding of free water to soap and 2) intensive mass shearing conditions to enhance the ordered layered structure. Such mass shearing conditions are believed to generate high extensional forces and can be accomplished by moving a perforated plate through the soap mass. In a preferred embodiment, iridescence of the bar is enhanced by sequential mixing which facilitates the preferential binding of water to the soap as opposed to water binding to the ethoxylated alcohol (or other hydrophilic components). In other words, all available sites of soap that can bind to water are saturated with water prior to adding the ethoxylated alcohol. This can also be expressed as the ratio of the total bound water to water that is bound to the soap being greater than 1.0. Bound water is herein defined as that water that is unavailable for binding to or solvating other hydrophilic materials formulated into the inventive soap bar such as but not limited to the ethoxylated alcohol. In a further preferred embodiment, additional shear is provided to the soap mass during the extrusion stage from e.g. a plastometer, followed by an equilibration stage after soap bar compression so as to produce a more intense iridescent effect.

The phenomena of iridescence in the continuous phase of the inventive soap bar is characterised as a blue hue whose intensity depends on the viewing angle. The perceived intensity of the blue hue also depends on the color and illumination of the surroundings. The inventive bar appearance is contrasted with the optical effects produced via the addition of iridescent pigments or particles (i.e. the dispersed phase) to prior art bars. Such dispersed phase particles produce both a qualitative and quantitative different optical appearance to that generated by the inventive continuous phase iridescent material. The degree of iridescence generated in the inventive soap bar (i.e. its continuous phase) was seen to vary as a function of free water content, the degree of alcohol ethoxylation, the ethoxylated alcohol concentration, and the ratio of alcohol concentration to ethoxylation degree and is discussed in further detail below. Irridescent, reflective, colored or other particles or blends thereof may be optionally added to the inventive soap bar.

SUMMARY OF THE INVENTION

In one aspect of the invention is a toilet bar having an iridescent continuous phase and an ordered, layered microstructure, including but not limited to:

a. at least 10% by wt. of a soap;

b. about 0.1 to about 20% by wt. of total C8 to C24 ethoxylated alcohol(s) with a ratio of methylene number to ethoxyl number in the range of 12 to 1.2;

c. wherein the ratio of ethoxylated alcohol(s) concentration to ethoxyl number is less than 2.3; and d. wherein the ratio of total bound water in the toilet bar to water bound to the soap is greater than 1.0.

In another aspect of the invention is a process for making the inventive iridescent soap bar including the steps of:

a. mixing fatty acid soap(s) with sufficient water to saturate all soap sites capable of complexing water until a uniform preblend is obtained;

b. adding the ethoxylated alcohol(s) to the uniform preblend formed in step (a);

c. mixing the product of step (b) in a high shear processor under conditions sufficient to impart a work level effective to produce an iridescent high shear blended product;

d. ejecting the blended product from the processor; and e. forming the ejected blended product into shaped soap bars.

DETAILED DESCRIPTION OF THE INVENTION

All publications and patent applications, patents, and other references mentioned herein are incorporated by reference in their entirety.

Figure 1:
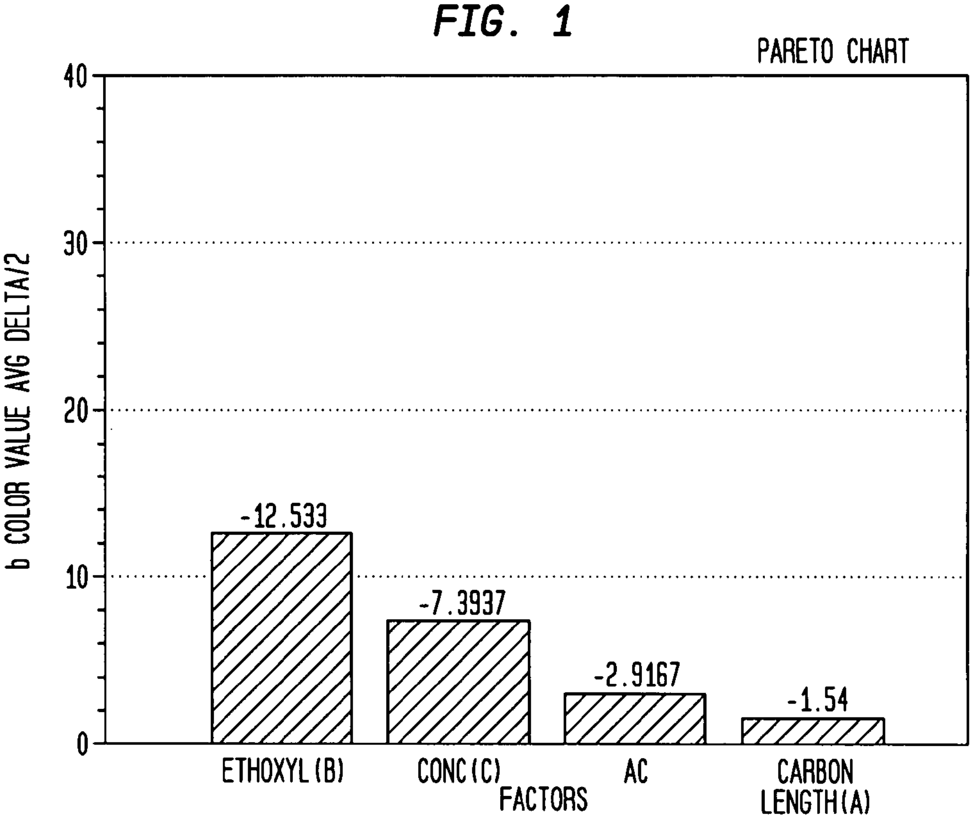
FIG. 1 is a Pareto Chart depicting the relationship between color value b and various ethoxylated alcohols formulated into various inventive and comparative soap bars.
Figure 2:
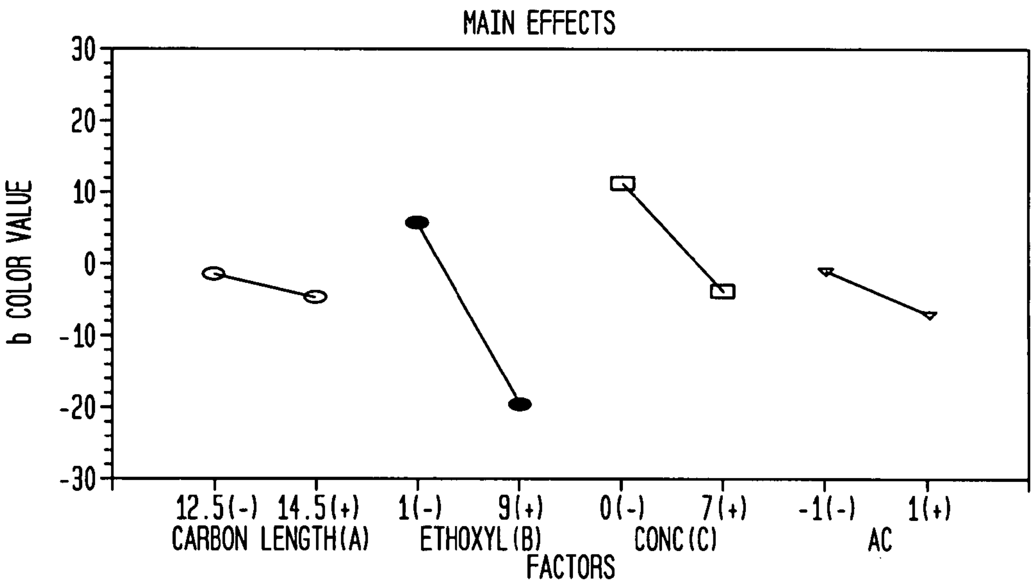
FIG. 2 is a main effects plot for color value b and defined Neodol® alcohol characteristics formulated into various inventive and comparative soap bars.

Referring now to the drawings in which like figures represent like elements, FIG. 1 depicts a Pareto Chart illustrating the relationship between color value b and different ethoxylated alcohols etc. formulated into inventive (1*a*, 2*a*, 3*a*, 4*a*, 5*a*, 6*a*, 8*a*, 9*a*, 13*a*1, 2*c*1, 1, 6) and comparative (7*a*, 10*a*, 11*a*, 12*a*, 2, 3, A1, A2) soap bars described in Table 1. FIG. 2 is a main effects plot for color value b and defined Neodol® alcohol characteristics formulated into the same toilet bars illustrated in FIG. 1. The Pareto Chart and main effects plot were both generated using Wisdom® design of experiments software as discussed below.

Figure 3:
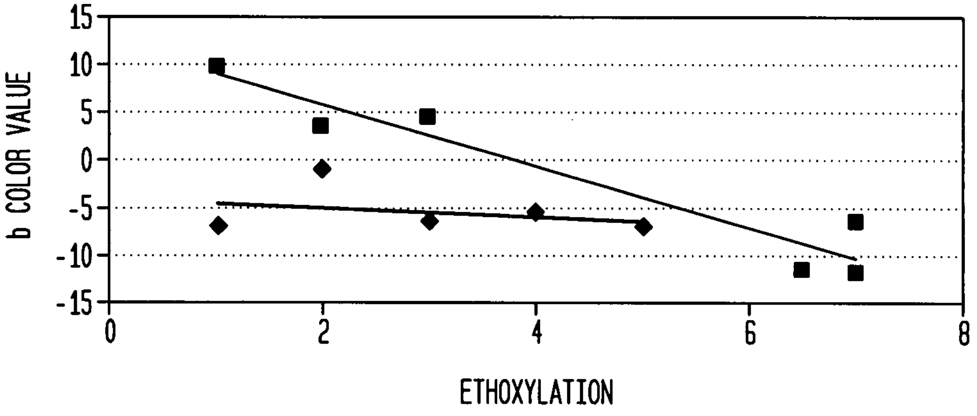
FIG. 3 depicts the relationship between b value and the degree of ethoxylation for various inventive and comparative soap bar formulas containing various Neodol® alcohols.

FIG. 3 depicts the relationship between b value and the degree of ethoxylation for various inventive and comparative soap bar formulas containing various Neodol® alcohols described in Table 1 and Table 2 inventive samples (9*a*, 6*a*, 11*a*, 2*a*, 13*a*1 represented as squares) and comparative samples (12*a*, 10*a*, 7*a* represented as diamonds).

Figure 4:
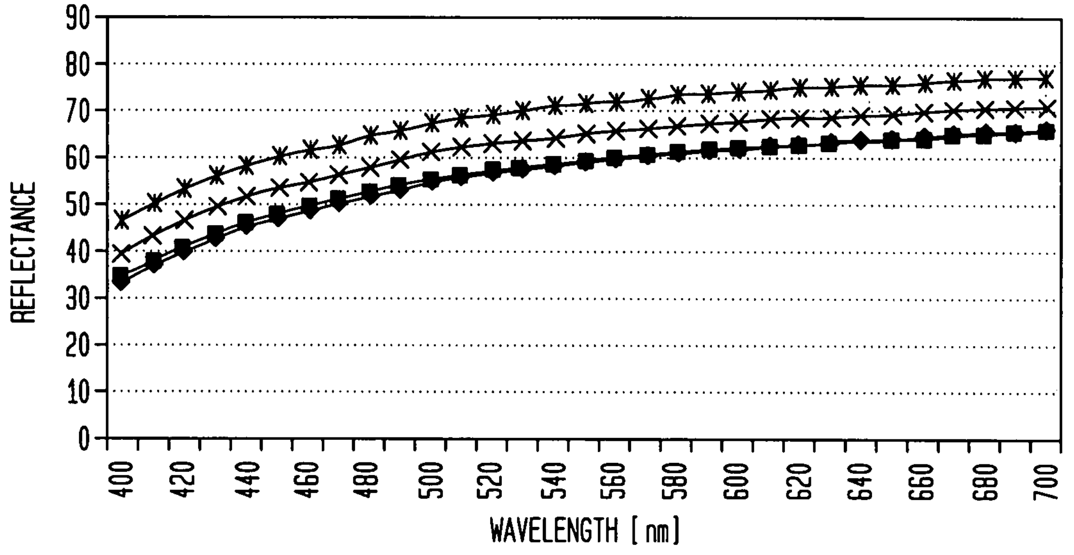
FIG. 4 depicts reflectance spectral data of a comparative white opaque soap bar sample at various viewing angles.

FIG. 4 depicts reflectance spectral data at various viewing angles of a comparative white opaque soap bar sample 10A described in Table 1. The viewing angles for FIGS. 4 and 5 are represented as follows: triangle for 110 degrees, diamond for 75 degrees, square for 45 degrees, x for 25 degrees and * for 15 degrees.

Figure 5:
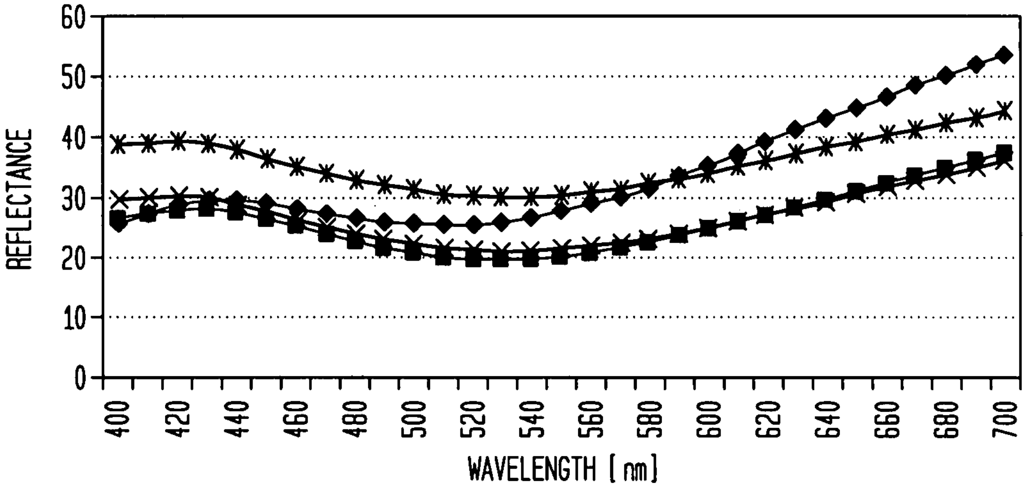
FIG. 5 depicts reflectance spectral data of an inventive iridescent soap bar at various viewing angles.

FIG. 5 depicts reflectance spectral data at various viewing angles of an inventive iridescent soap bar 4A described in Table 1.

Figure 6:
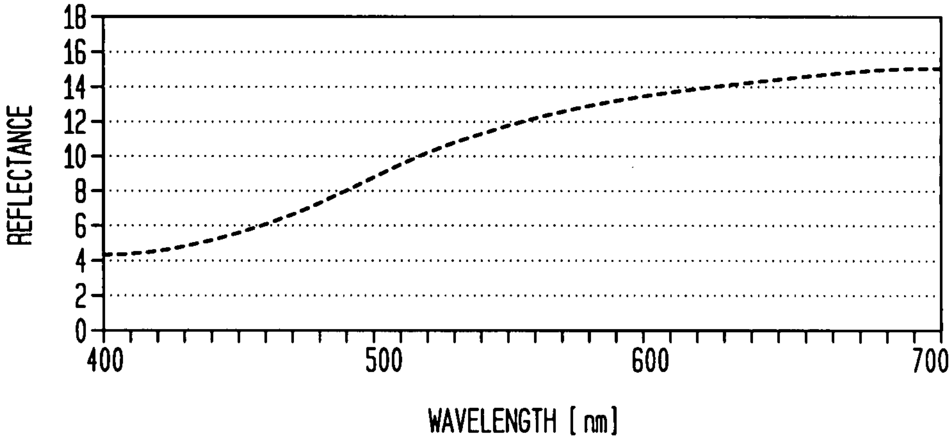
FIG. 6 depicts reflectance spectral data of a comparative translucent soap bar measured at a 45° angle.

FIG. 6 depicts reflectance spectral data measured at a 45° angle of a comparative translucent soap bar 7X described in Table 3.

Figure 7:
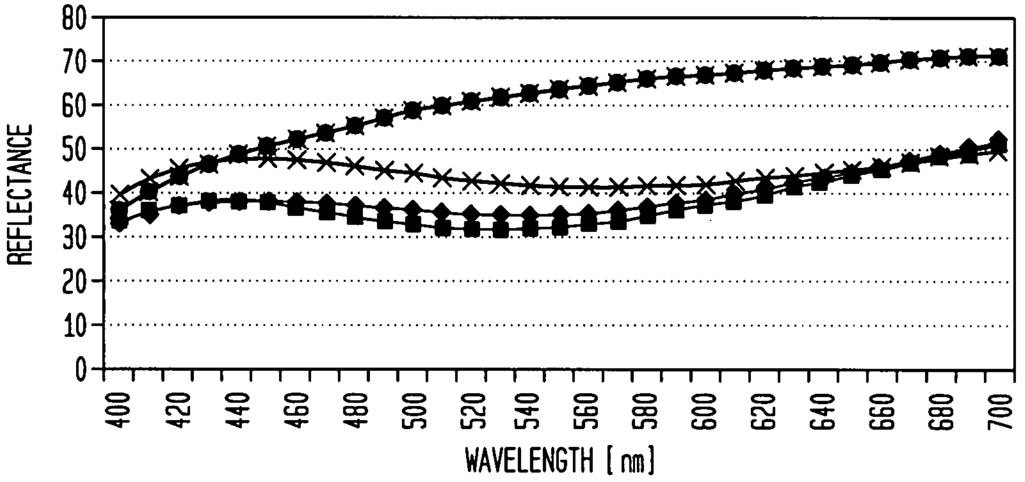
FIG. 7 depicts reflectance spectral data for various inventive iridescent and comparative non-iridescent soap bars at a 110° angle.

FIG. 7 depicts reflectance spectral data at a 110° angle for various inventive iridescent and comparative non-iridescent soap bars described in Table 1. The samples for FIGS. 7 and 8 are represented as follows: diamond for sample 1*a*, square for sample 3*a*, triangle for sample 4*a*, *x* for sample 6*a*, * for sample 9*a* and circle for sample 10*a*.

Figure 8:
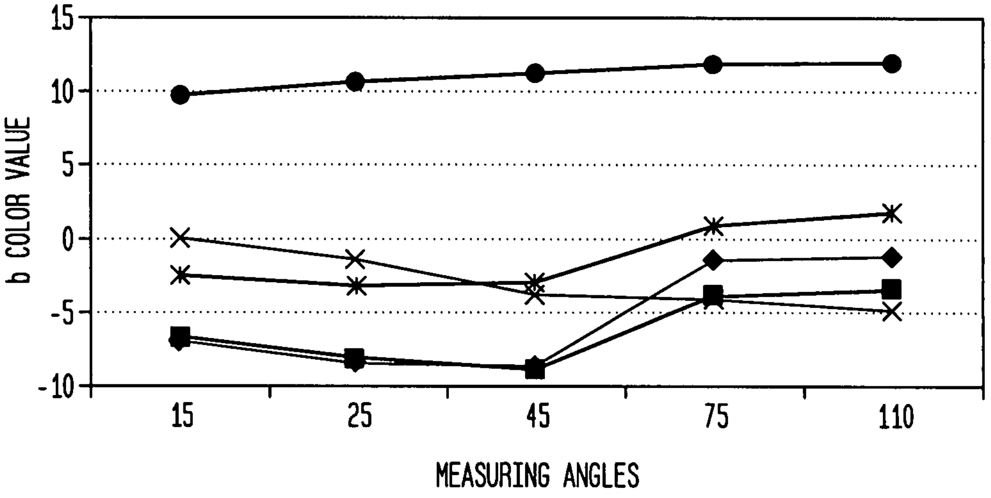
FIG. 8 depicts the b color value at different viewing angles for various inventive and comparative soap bars described in table 5.

FIG. 8 depicts the b color value at different viewing angles for different inventive and comparative formulations described in Table 1.

Figure 9:
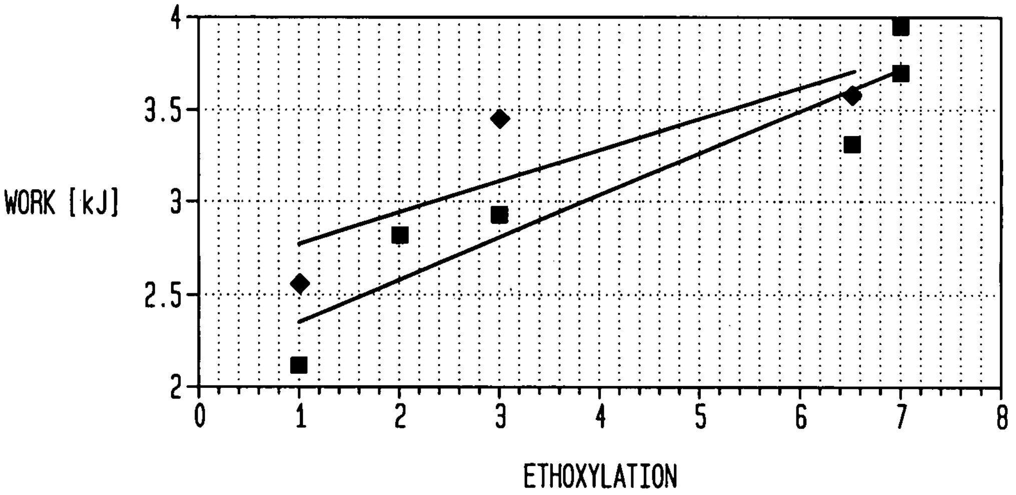
FIG. 9 depicts work necessary to mix soap-water-EA in stage II of mixing as a function of the degree of alcohol ethoxylation.

FIG. 9 depicts work necessary to mix soap-water-EA in stage II of mixing versus the degree of alcohol ethoxylation for various inventive samples 6, 6*a*, 9*a*, 4*a*, & 2*a* represented as diamonds and comparative samples 3, 10*a*, 7*a*, & 12*a* represented as squares. The samples are further described in Table 1.

Figure 10:
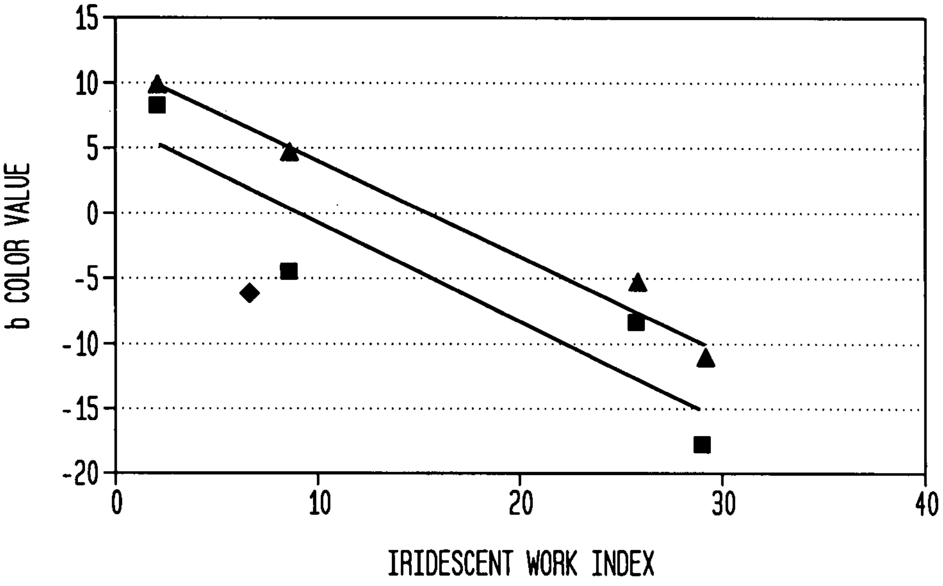
FIG. 10 depicts the relationship between Iridescent work index and color value b.

FIG. 10 depicts the graphical relationship between Iridescent work index and color value b for various inventive and comparative soap bars described in Table 1. Samples 2, 2*a*, 1*a*, 5*a*, & 8*a* are represented by triangles or diamonds and samples 13*a*1, 7*a*, 10*a* & 11 *a* are represented by squares.

Figure 11:
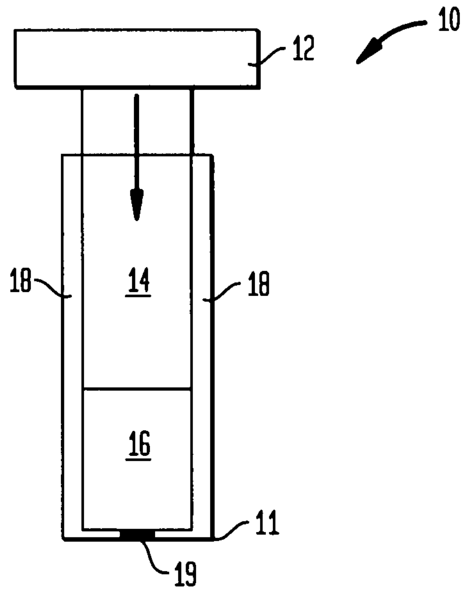
FIG. 11 is a schematic cross-sectional view of a plastometer.

Now referring to FIG. 11, a suitable plastometer 10 for preparing the inventive soap bar consists of a cylinder 11 adapted for receiving a predetermined quantity of soap 16. Piston 14 is pressed against soap 16 via a pneumatic or mechanical ram or equivalent device (not shown) and the force of compression of the piston is measured by load cell 12 and may be suitably adjusted to a predetermined pressure. Cylinder 11 has jacketed walls 18 in which a liquid whose temperature is thermostatically controlled may be circulated so as to control the temperature of soap 16 during its residence time in cylinder 11. Plug 19 is secured in place while simple compression of soap 16 is applied and is removed when transfer of soap 16 from the plastometer 10 via extrusion is desired.

Figure 12:
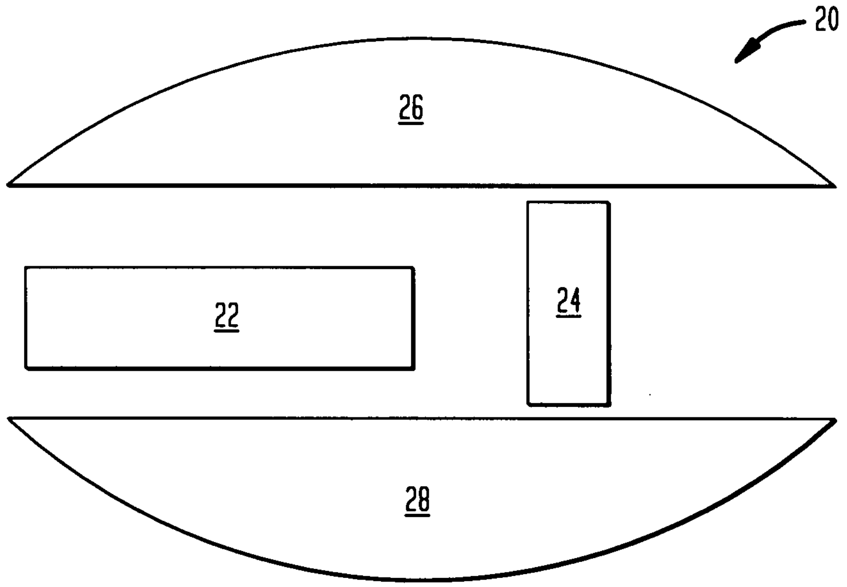
FIG. 12 is a schematic cross-sectional view of a pneumatic stamper.

Now referring to FIG. 12, a pneumatic stamper 20 for stamping shaped bars from a soap billet 22 or 24, such as that prepared in the plastometer illustrated in FIG. 11, consists of an upper die 26 and a lower die 28 arranged to compress the soap billet to form a shaped soap bar. The soap billet may be stamped either parallel to the axis of compression of the soap mass in the plastometer (see FIG. 11) as illustrated schematically by billet 22 or stamped normal to the axis of compression of the soap mass as illustrated schematically by billet 24. Billets 22 and 24 are arranged adjacent to each other in FIG. 14 for illustrative purposes only.

Figure 13A:
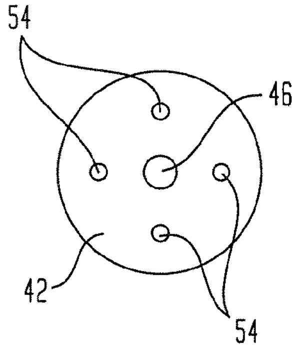
FIG. 13*a* is a detailed top plan view of plate 42 depicted in FIG. 13.
Figure 13:
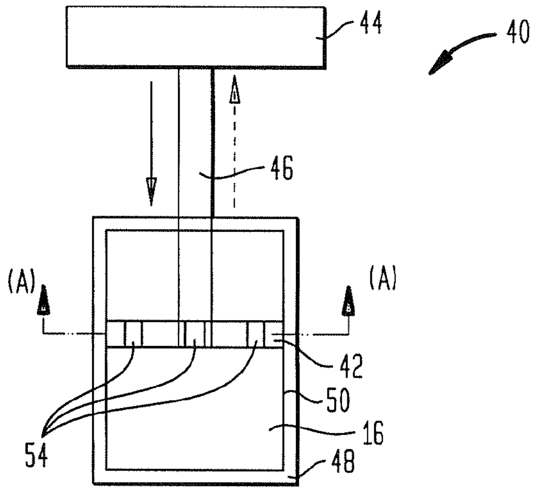
FIG. 13 is a schematic cross-sectional view of a lab intensive mixer.

Referring now to FIGS. 13 and 13(*a*), a lab intensive mixer 40 suitable for preparing the inventive bar consists of a housing 48 and perforated plate 42 having a plurality of holes 54, the plate 42 being rigidly attached to a movable rod 46 connected to a drive mechanism (not shown). In operation, plate 42 moves in reciprocating back and forth motion within housing 48 and in close proximity to housing walls 50 while contacting soap material 16 and wherein the soap 16 is first extruded through holes 54 in one direction and extruded in the opposite direction as plate 42 returns to its original position in housing 48. This results in the soap 16 undergoing high shear mixing conditions for a predetermined number of back and forth cycles of plate 42. The speed of the plate 42 may be varied for greater or lesser shear mixing in a predetermined manner.

Figure 14:
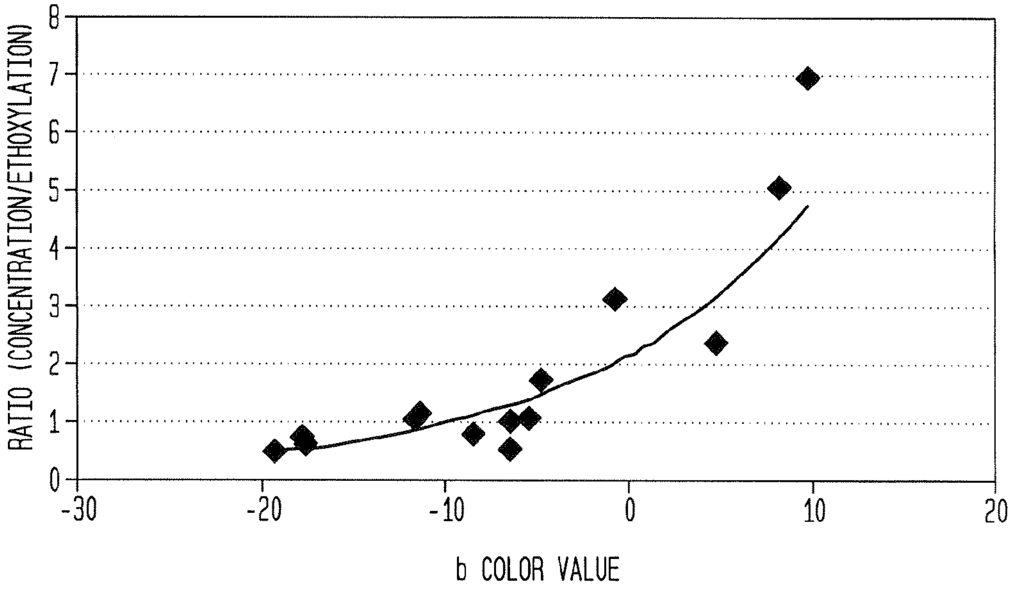
FIG. 14 depicts the graphical relationship of b value to the ratio of ethoxylated alcohol concentration to ethoxyl number for various inventive and comparative soap bars.

FIG. 14 depicts the graphical relationship of b value to the ratio of ethoxylated alcohol to ethoxyl number for various inventive (9*a*, 6*a*, 3*a*, 2C1, 8*a*, 5*a*, 1*a*, 4*a*, 2*a*, 13*a*1) and comparative (12*a*, 11*a*, 10*a*, 7*a*) soap bars described in Table 1.

In one aspect of the invention is a toilet bar having an iridescent continuous phase and an ordered, layered microstructure, including but not limited to:

a. at least 10% by wt. of a soap; (preferably at least 40% by wt.; more preferably at least 50% by wt. and most preferably at least 60% by wt. of soap)

b. about 0.1 to about 20% by wt. of total C8 to C24 ethoxylated alcohol(s) with a ratio of methylene number to ethoxyl number in the range of 12 to 1.2; (preferably having a maximum ratio of 11, 10, 9, or 8 within this range);

c. wherein the ratio of ethoxylated alcohol(s) concentration to ethoxyl number is less than 2.3; and d. wherein the ratio of total bound water in the toilet bar to water bound to the soap is greater than 1.0 (preferably the bound water in the toilet bar will be in excess of total water capable of forming soap-water complexes under standard conditions (e.g. blending a 10% by wt. stoichiometric excess of water with soap for 1 hrs at 50 C); more preferably the total water content is greater than about 16, 22 or 25% by wt. based on the dry wt. of soap).

Advantageously the inventive toilet bar contains one or more C11 to C15 ethoxylated alcohol(s) having between 2 to 10 moles of ethoxylation. Preferably the ethoxylated alcohols are present in the concentration range of about 0.1 to 9% by wt. (more preferably 2 to 8% by wt. and most preferably 3 to 7% by wt.)

In a preferred embodiment the bar has a yield stress value from about 15 Kpa to 800 KPa at 25° C. and 50% RH. Preferably the bar has been processed with a quantity of work of mixing equivalent to an Iridescence Work Index of at least 5 (preferably at least 6.7, and more preferably at least 10).

Advantageously the inventive bar contains about 40 to about 85% by wt. of a C6 to C22 fatty acid soaps; (preferably 39 to 85% by wt. of a C6 to C22; more preferably 51 to 76% by wt. of a C6 to C22 and most preferably 60 to 76% by wt. of C12 to C18 fatty acid soaps). Preferably the bar further includes about 3 to 22% by wt. of total water (preferably in the range of 4, 5 or 6% by wt. to 16 or 18% by wt. of water).

In a preferred embodiment, the bar shows a substantially blue iridescence characterized by a b* measurement of −1 or less using the standard L a b Color Space method.

Preferably, the soap bar further includes 0 to about 20% by wt. of a synthetic anionic surfactant. (preferably up to a maximum level of 10% by wt.). More preferably the synthetic anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof.

In another aspect of the invention is a process for making the inventive iridescent soap bar including the steps of:

a. mixing fatty acid soap(s) with sufficient water to saturate all soap sites capable of complexing water until a uniform preblend is obtained;

b. adding the ethoxylated alcohol(s) to the uniform preblend formed in step (a);

c. mixing the product of step (b) in a high shear processor under conditions sufficient to impart a work level effective to produce an iridescent high shear blended product;

d. ejecting the blended product from the high extension shear processor; and e. forming the ejected blended product into shaped soap bars.

Advantageously the quantity of work level used in the process is equivalent to an Iridescence Work Index of at least 5 (preferably with a maximum of 6.7, and most preferably 10). Preferably the preblend is further processed with a high extension shear mixer. More preferably the ejected blended product is additionally compressed, (optionally allowed to relax), extruded then stamped or extruded then cut to obtain shaped inventive soap bars.

Surfactants:

Surfactants, also known as detergents, are an essential component of the inventive toilet bar composition. They are compounds that have hydrophobic and hydrophilic portions that act to reduce the surface tension of the aqueous solutions they are dissolved in. Useful surfactants include soap(s), and non-soap anionic, nonionic, amphoteric, and cationic surfactant(s), and blends thereof.

Anionic Surfactants:

The inventive toilet bar composition optionally contains one or more non-soap anionic detergent(s) (syndets). Advantageously such non-soap anionic detergent(s) or surfactant(s) may be used up to 20%, preferably to a maximum level of 10% by wt.

The anionic detergent active which may be used may be aliphatic sulfonate(s), such as a primary alkane (e.g., $C_8$-$C_{22}$) sulfonate(s), primary alkane (e.g., $C_8$-$C_{22}$) disulfonate(s), $C_8$-$C_{22}$ alkene sulfonate(s), $C_8$-$C_{22}$ hydroxyalkane sulfonate(s) or alkyl glyceryl ether sulfonate(s) (AGS); or aromatic sulfonate(s) such as alkyl benzene sulfonate.

The anionic may also be alkyl sulfate(s) (e.g., $C_{12}$-$C_{18}$ alkyl sulfate) or alkyl ether sulfate (including alkyl glyceryl ether sulfates). Among the alkyl ether sulfate(s) are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinate(s) (including mono- and dialkyl, e.g., $C_6$-$C_{22}$ sulfosuccinate(s)); alkyl and acyl taurate(s), alkyl and acyl sarcosinate(s), sulfoacetate(s), $C_8$-$C_{22}$ alkyl phosphate(s) and phosphate(s), alkyl phosphate ester(s) and alkoxyl alkyl phosphate ester(s), acyl lactate(s), $C_8$-$C_{22}$ monoalkyl succinate(s) and maleate(s), sulphoacetate(s), and alkyl glucoside(s) and the like.

Sulfosuccinates may be monoalkyl sulfosuccinates having the formula:

$R^4O_2CCH_2CH(SO_3M)CO_2M$; and amide-MEA sulfosuccinates of the formula;

$R^4CONHCH_2CH_2O_2CCH_2CH(SO_3M)CO_2M$ wherein $R^4$ ranges from $C_8$-$C_{22}$ alkyl and M is a solubilizing cation.

Sarcosinates are generally indicated by the formula:

$R^1CON(CH_3)CH_2CO_2M$, wherein $R^1$ ranges from $C_8$-$C_{20}$ alkyl and M is a solubilizing cation.

Taurates are generally identified by formula:

$R^2CONR^3CH_2CH_2SO_3M$ wherein $R^2$ ranges from $C_8$-$C_{20}$ alkyl, $R^3$ may be H or $C_1$-$C_4$ alkyl and M is a solubilizing cation.

Monoacyl and/or diacyl C8-C18 isethionate surfactants having the general formula:

$RC—O(O)—CH_2—CH_2—SO_3M^+$ or $(RC—O(O)—CH_2—CH_2—SO_3)_2M^{++}$ wherein R is an alkyl group having 8 to 18 carbons, and M is a mono or divalent cation such as, for example, sodium, potassium, ammonium, calcium and magnesium or other mono and divalent cations may be used. Preferably the isethionates have an average iodine value of less than 20.

Fatty Acid Soap

The inventive toilet bar composition contains soap. The term "soap" is used here in its popular sense, i.e., the alkali metal or alkanol ammonium salts of aliphatic alkane- or alkene monocarboxylic acids preferably having about 6 to 22 carbon atoms, more preferably about 6 to about 18 or about 12 to 18 carbon atoms. They may be further described as alkali metal carboxylates of aliphatic hydrocarbons. Sodium, potassium, mono-, di- and tri-ethanol ammonium cations, or combinations thereof, are suitable for purposes of this invention. In general, sodium soaps are used in the compositions of this invention, but from about 1% to about 25% of the soap may be potassium soaps. The soaps may contain unsaturation in accordance with commercially acceptable standards. Excessive unsaturation is normally avoided to minimize color and odor issues. Advantageously soap may be used in the range of about 20, 30 or 40 to 85% by wt., preferably about 39 to 85%, more preferably about 51 to 76% by wt., and most preferably about 60 to 76% by wt.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Amphoteric Surfactants

One or more amphoteric surfactant(s) may be optionally used in this invention. Advantageously such amphoteric surfactant(s) may be used up to 20% by wt., preferably to a maximum level of 10% by wt.

Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1—[—C(O)—NH(CH_2)_n—]_m—N^+—(R^2)(R^3)X—Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $—CO_2—$ or $—SO_3—$

Suitable amphoteric surfactants within the above general formula include simple betaines of formula:

$$R^1—N^+—(R^2)(R^3)CH_2CO_2^-$$

and amido betaines of formula:

$$R^1—CONH(CH_2)_n—N^+—(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1—N^+—(R^2)(R^3)(CH_2)_3SO_3^-$$

or $$R^1—CONH(CH_2)_m—N^+—(R^2)(R^3)(CH_2)_3SO_3^-$$

where m is 2 or 3, or variants of these in which $—(CH_2)_3SO_3^-$ is replaced by $$—CH_2C(OH)(H)CH_2SO_3^-$$

In these formulae $R^1$, $R^2$ and $R^3$ are as discussed previously.

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

One or more nonionic surfactants may also be optionally used in the toilet bar composition of the present invention. Advantageously such nonionic surfactant(s) may be up to a maximum level of about 10, 5, or 2% by wt.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses or polyquarterium compounds.

Advantageously cationic skin feel agent(s) or polymer(s) are used from about 0.01, 0.1 or 0.2% by wt. to about 1, 1.5 or 2.0% by wt. in the inventive toilet bars.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogen ides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred skin cleansing embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment.

Cationic Surfactants

One or more cationic surfactants may also be used in the inventive toilet bar composition. When desired, cationic surfactants may be used from about 0.1, 0.5 or 1.0% by wt. to about 1.5, 2.0 or 2.5% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar., 27, 1973; and "Surface Active Agents and Detergents" (Vol. I & II) by Schwartz, Perry & Berch, both of which are also incorporated into the subject application by reference.

Exfoliants

The inventive toilet bar may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table A below. Advantageously such exfoliants may be present at a level of less than 1% by wt.

TABLE A

| Material | Hardness (Mohs) |
|---|---|
| Talc | 1 |
| Calcite | 3 |
| Pumice | 4-6 |
| Walnut Shells | 3-4 |
| Dolomite | 4 |
| Polyethylene | ~1 |

Miscellaneous Ingredients

In addition, the toilet bar composition of the invention may include 0 to about 15% by wt. optional ingredients as follows: sequestering agents, such as tetrasodium ethylenediaminetetraacetate (EDTA), EHDP or mixtures in an amount of about 0.01 to 1%, preferably about 0.01 to 0.05%. Perfumes may be included at levels of less than about 2, 1, 0.5 or preferably less than about 0.3, 0.2 or 0.1% by wt.

The compositions may further comprise preservatives such as dimethyloldimethylhydantoin (Glydant XL1000), parabens, sorbic acid etc., and the like. The compositions may also comprise coconut acyl mono- or diethanol amides as suds boosters, and strongly ionizing salts such as sodium chloride and sodium sulfate may also be used to advantage. Antioxidants such as, for example, butylated hydroxytoluene (BHT) and the like may be used advantageously in amounts of about 0.01% or higher if appropriate.

Skin Conditioning Agents

Skin conditioning agents such as emollients are advantageously used in the present invention for personal toilet bar compositions. Hydrophilic emollients including humectants such as polyhydric alcohols, e.g. glycerin and propylene glycol, and the like; polyols such as the polyethylene glycols listed below, and the like and hydrophilic plant extracts may be used. Advantageously such humectants may be used to a maximum of 20% by wt., preferably to a level of 10% by wt., and more preferably to a level of 5% by wt.

| | |
|---|---|
| Polyox WSR-205 | PEG 14M, |
| Polyox WSR-N-60K | PEG 45M, or |
| Polyox WSR-N-750 | PEG 7M. |

Hydrophobic emollients may be used in the inventive toilet bar. Advantageously such hydrophobic emollients may be used to a maximum of 10%, most preferably to a maximum level of 8%, most preferably to a maximum level of 5%.

The term "emollient" is defined as a substance which softens or improves the elasticity, appearance, and youthfulness of the skin (stratum corneum) by increasing its water content, and keeps it soft by retarding the decrease of its water content.

Useful hydrophobic emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;
(d) hydrophobic plant extracts;
(e) hydrocarbons such as liquid paraffin, petrolatum, microcrystalline wax, ceresin, squalene, pristan and mineral oil;
(f) higher fatty acids such as lauric, myristic, palmitic, stearic, behenic, oleic, linoleic, linolenic, lanolic, isostearic, arachidonic and poly unsaturated fatty acids (PUFA);
(g) higher alcohols such as lauryl, cetyl, stearyl, oleyl, behenyl, cholesterol and 2-hexydecanol alcohol;
(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;
(i) essential oils and extracts thereof such as *mentha*, jasmine, camphor, white cedar, bitter orange peel, ryu, turpentine, cinnamon, bergamot, *citrus unshiu*, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, *calendula*, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; and
(j) mixtures of any of the foregoing components, and the like.

Preferred hydrophobic emollient moisturizing agents are selected from fatty acids, di and triglyceride oils, mineral oils, petrolatum, silicone oils, and mixtures thereof; with fatty acid(s) being most preferred for the toilet bar. Advantageously such fatty acid(s) may be used to a maximum level of 10% by wt., most preferably to a maximum level of 5% by wt.

Iridescent Bar Processing

Making the inventive bar can be divided into three sequential processing stages: a. mixing (e.g. via the intensive mixer), b. material compression (e.g. plastometer) and c. extrusion (e.g. plastometer) and the process parameters of each of these stages may be varied to enhance bar iridescence. Application of intensive extensional shear conditions during mixing and extrusion was seen to enhance bar iridescence. Separating the mixing process of the inventive bar into two consecutive stages, i.e. mixing of soap and water only in the first stage and the addition of the ethoxylated alcohols in the second stage with further mixing is important to enhance iridescence in a preferred embodiment.

It was also observed that the work (joules) ("a") required to mix soap-water-ethoxylated alcohols is roughly proportional to both the degree of alcohol ethoxylation ("b") and alcohol concentration (see FIG. 9).

The product of the two expressions (a*b) is defined herein as the Iridescence Work Index. The Iridescence Work Index is found to be roughly proportional to blue hue generated in the soap mass (see FIG. 10).

Other effects were noted with respect to detecting the iridescent effect of the bar. Translucency appears to intensify apparent iridescence to an observer and less translucent compositions show more of an opalescent (pearly) effect. Opalescence is a subspecies of iridescence as discussed above.

When the soap is processed at lower speed (i.e. lower shear rate), the number of cycles (i.e. piston transits of the intensive mixer), is less critical to the formation of blue iridescence than when the processing is conducted at higher speed (i.e. higher shear rate). The more cycling of the formula, at higher speed, the more blue iridescent effect is generated in the product.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Soap compositions were formulated according to Table 1 and their appearance was assessed using three instrumental methods: (i) color value expressed as L, a, b; (ii) opacity, and (iii) reflectance spectral characteristics at various viewing angles using the methods described below.

TABLE 1A

Opacity and Color analysis of inventive and comparative soap bars.

| Sample | Alcohol Neodol ® (1) type | Alcohol conc. % w/w | Ave. opacity [%] (std. dev) | Ratio of alcohol conc. To eo number | L* | a* | Ave. b value (std. dev) (2) or observable iridescence detected |
|---|---|---|---|---|---|---|---|
| 1a (Inv.) | 25-7 | 5.10 | 90.6 (1.4) | 0.73 | 53.5 | −3.0 | −17.8 (0.9) |
| 2a (Inv.) | 25-7 | 7.00 | 99.9 (4.9) | 1.0 | 51.9 | −2.1 | −6.3 (0.3) |
| 2a (replicate) (Inv.) | 25-7 | 7.00 | 92.6 (1.3) | 1.0 | 50.3 | −1.8 | −5.6 (0.9) |
| 3a (Inv.) | 25-7 | 4.12 | 87.8 (1.0) | 0.59 | 48.7 | 0.6 | −17.6 (1.6) |
| 4a (Inv.) | 23-6.5 | 7.00 | 97.7 (5.4) | 1.08 | 52.3 | 0.1 | −11.3 (2.3) |
| 5a (Inv.) | 23-6.5 | 5.10 | 96.9 (1.6) | 0.78 | 59.9 | −2.5 | −8.4 (3.1) |
| 6a (Inv.) | 23-6.5 | 3.13 | 97.1 (2.4) | 0.48 | 63.2 | −2.6 | −6.3 (2.5) |
| 7a (Comp.) | 25-3 | 7.00 | 99.5 (1.1) | 2.33 | 78.9 | −3.2 | 4.7 (0.6) |
| 8a (Inv.) | 25-3 | 5.10 | 98.8 (0.2) | 1.7 | 70.9 | −5.7 | −4.6 (0.4) |
| 9a (Inv.) | 25-3 | 3.13 | 99.0 (0.4) | 1.04 | 72.0 | −7.7 | −5.3 (0.7) |
| 10a (Comp.) | 23-1 | 7.00 | 99.7 (1.2) | 7.00 | 83.2 | −3.3 | 9.7 (0.3) |
| 11a (Comp.) | 23-1 | 5.10 | 99.2 (1.1) | 5.10 | 83.2 | −3.0 | 8.1 (0.2) |
| 12a (Comp.) | 23-1 | 3.13 | 99.6 (0.3) | 3.13 | 77.2 | −7.0 | −0.8 (0.5) |

TABLE 1A-continued

| Opacity and Color analysis of inventive and comparative soap bars. | | | | | | | |
|---|---|---|---|---|---|---|---|
| Sample | Alcohol Neodol ® (1) type | Alcohol conc. % w/w | Ave. opacity [%] (std. dev) | Ratio of alcohol conc. To eo number | L* | a* | Ave. b value (std. dev) (2) or observable iridescence detected |
| 13a1 (Inv.) | 45-7 | 7.00 | 92.6 (1.5) | 1.00 | 51.6 | −1.3 | −11.7 (1.2) |
| 2c1 (Inv.) | 25-9 | 4.12 | 99.6 (0.6) | 0.46 | 30.3 | 21.1 | −19.4 (1.2) |
| 1 (Inv.) | 45-2 | 4 | 80.7 | 2 | | | −6.8 |
| 2 (Comp.) | 45-2 | 5 | 97 | 2.5 | | | 3.8 |
| 3 (Comp.) | 45-2 | 7 | 97 | 3.5 | | | 3.5 |
| 4 (Inv.) | 45-7 | 3 | | .43 | | | Blue iridescence observed |
| 5 (Inv.) | 45-7 | 5 | | .43 | | | Blue iridescence observed |

TABLE 1B

| Opacity and Color analysis of inventive and comparative soap bars. Effect of process conditions for specified samples: i.e. number of intensive mixer cycles and speed of mixing (shear). | | | | | | | |
|---|---|---|---|---|---|---|---|
| Sample | Alcohol (Neodol ®) type (1) | Alcohol conc. % w/w | Ave. opacity [%] (std. dev) | Ratio of alcohol conc. To eo number | L* | a* | Ave. b value (std. dev) (2) |
| 10 cycles @ 500 mm/min (Inv.) | 145b-2 | 4.12 | 80.6 (2.7) | 2.06 | 62.2 | −2.7 | −2.2 (0.9) |
| 20 cycles @ 500 mm/min (Inv.) | 145b-2 | 4.12 | 77.0 (1.4) | 2.06 | 62.7 | −3.2 | −6.1 (1.0) |
| 30 cycles @ 500 mm/min (Inv.) | 145b-2 | 4.12 | 75.1 (0.8) | 2.06 | 59.7 | −1.8 | −5.7 (0.5) |
| 40 cycles @ 500 mm/min (Inv.) | 145b-2 | 4.12 | 80.7 (0.9) | 2.06 | 62.0 | −4.3 | −6.8 (0.8) |
| 10 cycles @ 50 mm/min (Inv.) | 25-9 | 4.12 | 78.1 (1.6) | 0.46 | 59.9 | −3.3 | −5.2 (0.7) |
| 20 cycles @ 50 mm/min (Inv.) | 25-9 | 4.12 | 86.7 (1.2) | 0.46 | 66.3 | −5.9 | −5.1 (0.4) |

Notes:

(1) Neodol ® alcohols are ethoxylated alcohols supplied by Shell Chemical (Houston, TX). Other ethoxylated alcohols having similar alkyl chain distribution and eo number may be used such as those available from Sasol Corp.

(2) The more negative the b value the more blue the material appears to the observer. Conversely, the higher or more positive the b value the more yellow the material appears to the observer.

TABLE B

| Molecular structures of selected Neodol ® alcohols: | | | |
|---|---|---|---|
| Alcohol (Neodol ®*) type | Alkyl chain distribution | Number of EO groups | Ratio of ave. methylene no. to EO groups |
| 25-7 | C12, C13, C14 & C15 | 7 | 1.9 |
| 23-6.5 | C12 & C13 | 6.5 | 1.9 |
| 25-3 | C12, C13, C14 & C15 | 3 | 4.8 |
| 23-1 | C12 & C13 | 1 | 12.5 |
| 45-7 | C14 & C15 | 7 | 1.9 |
| 145b-2 | C11, C14 & C15 | 2 | 6.6 |
| 25-9 | C12, C13, C14 & C15 | 9 | 1.5 |
| 45-2 | C14 & C15 | 2 | 7.2 |

Values of b above 0 indicate yellow color. Blue color is barely visible to the observer between 0 and −1 and noticeably visible below −1. A strong blue color is apparent to the observer below −10. The intensity of blue and yellow hue will also depend on redness and lightness of the sample. Variables affecting visual observations include level of illumination, color of illumination, size, presence of gloss on specimen, surroundings and background, etc. A more detailed description of these effects is described in *The Measurement of Appearance*, R. Hunter, R. Harold, published by Wiley-Interscience, $2^{nd}$ edition, 1987.

To an observer, the intensity of blue color appearing in the soap is indicative of its iridescence and was confirmed and quantified by the instrumental methods described below. Blue hue intensity was found to vary with concentration and type of ethoxylated alcohol. Some ethoxylated alcohols show a negligible effect on iridescence (e.g. Neodol® 23-1) and some show a strong effect (e.g. Neodol® 25-7). The smaller the ratio of concentration to ethoxylation number, the more iridescent the soap (see FIG. 14).

The color effect visible in small 1 cm soap pellets reported in Tables 1A&B is also visible in a finished conventional size soap bar (e.g. 5 cm width by 8 cm in length by 3 cm in thickness). Samples of conventional sized soap bars were prepared from 5-6 cm long soap plugs (1 cm diameter) with a plastometer illustrated in FIG. 11. The soap plugs were then manually compressed and stamped using a conventional pneumatic actuated stamper illustrated in FIG. 12.

To determine if stamping orientation has an effect on perceived color, the soap plugs were arranged on the stamper platen in a parallel or separately in a perpendicular orientation to the axis of extrusion (illustrated in FIG. 12). It was observed that there is a difference in color intensity between the two stamping orientations. Iridescence appears stronger in the parallel direction by observation.

The dependency between ethoxylated alcohols of varying average alkyl chair length and eo number and measured iridescence was analyzed using Wisdom Design of Experiments software (Version 6.1.1.) available from Launsby Consulting, (Colorado Springs, Colo.). The following factors were studied: average carbon chain length (A), ethoxylation degree (B), Neodol® concentration (C), and their interactions: BC, AC, AB and ABC.

Ethoxylation, carbon chain length and concentration were plotted against the intensity of blue color. Pareto Chart and Main effects plots were prepared as calculated for all samples shown in Table 1A which had a numerical b value and samples A1 and A2 from Table 2. These are shown in FIGS. 1 and 2, respectively. It was observed that blue intensity depended on the degree of ethoxylation of the Neodol® alcohol employed and its concentration. The alcohol chain length appeared less important since each of the alcohols tested in the examples is a mixture of at least two carbon chains and the maximum difference between the shortest and the longest alcohol studied was five methylene units. Interaction between alcohol concentration and carbon chain length seemed to be slightly more important than the carbon chain length itself.

FIG. 3 depicts the relationship between b value and the degree of ethoxylation for various Neodol® alcohols. Two concentrations, 3% and 7%, of various Neodol® types are plotted there. One observes that as the degree of ethoxylation increases the b value becomes more negative. This is apparent for the 7% level but less apparent for 3% level.

EXAMPLE 2

The effects of a) varying processing conditions and b) the use of additives such as glycerine on iridescence and color of selected soap compositions of Example 1 were studied and are summarized in Table 2. Table 2 also lists information about formula processing. Soap bars B7 and B8 were prepared to evaluate the importance of sequential mixing where B7 represents sequential mixing (to maximize water binding to soap) and B8 is an example of mixing all components at once (where there is insufficient water to bind to all available sites for the soap). Similarly samples A5 and A6 has all components mixed at once and samples A3 and A4 represent sequential mixing to maximize water binding to soap.

TABLE 2

Iridescence and opacity results for soap formulations under different processing conditions and with varying levels of added glycerine.

| Sample | Neodol ® or other alcohol type | 85/15 soap (% by wt.) | Additional Water (6) (% by wt.) | Neodol ® alcohol (% by wt.) | Ratio of alcohol conc. To eo number | Opaque (white) or translucent | Observable iridescence. |
|---|---|---|---|---|---|---|---|
| A1 (Comp.) | — | 96 | 4 | 0 | — | white | No |
| A2 (Comp.) | — | 84 | 16 | 0 | — | Partly white | No |
| A3 (Inv.) (1)* | 25-9 | 90 | 5 | 4 | 0.44 | translucent | Yes |
| A4 (Inv.) (1)** | 25-9 | 90 | 5 | 4 | 0.44 | translucent | Yes |
| A5 (Comp.) (5) | 25-9 | 80 | 10 | 7 | 0.78 | white | no |
| A6 (Comp.) (5) | 25-9 | 84 | 16 | 3 | 0.34 | white | No |
| B1A (Inv.) (2) | 25-9 | 88 | 6.3 | 5.75 | 0.64 | translucent | yes |
| B1B (Inv.) (3) | 25-9 | 88 | 6.3 | 5.75 | 0.64 | translucent | Yes (>bluer than B1A) |
| B9 (Inv.) | 25-9 | 88 | 10 | 2 | 0.22 | translucent | Slight |
| B2 (Inv.) (1)*** | 25-9 | 88 | 5.2 | 7 | 0.78 | translucent | yes |
| B3 (Inv.) | 25-9 | 88 | 10 | 2 | 0.22 | translucent | Slight |
| B5 (Inv.) | 25-9 | 88 | 5 | 7 | 0.78 | translucent | yes |
| B6 (Inv.) | 25-9 | 88 | 8.8 | 3.25 | 0.36 | translucent | Slight |
| B7 (Inv.) | 25-9 | 88 | 7.5 | 4.5 | 0.50 | translucent | Slight |
| B8 (Comp.) (5) | 25-9 | 88 | 7.5 | 4.5 | 0.50 | white | no |
| C1 (Comp.) | glycerine | 88 | 10 | | — | translucent | negligible |
| C2 (Comp.) | glycerine | 88 | 7.9 | | — | translucent | no |
| C3 (Inv.) | glycerine/ Neodol ® 25-9 | 86 | 10 | 2 | 0.22 | translucent | yes |
| 15-117-20 (Inv.) (7) | 25-9 | | | 7 | 0.78 | | yes |
| 15-117-6 (Comp.) (7) | 25-7 | 90 | 5 | 4 | 0.57 | white | no |

Notes:

Glycerine was added in samples C1, C2 and C3 at concentrations OF 2, 3.3 and 2% by wt. respectively.

(1) number of cycles for soap-water mixing: *1 cycle, 25 cycles, *50 cycles (2) soap - water mixing with 2 cycles then Neodol ® addition and mix 25 cycles (3) soap - water mixing with 2 cycles then Neodol ® addition and mix 50 cycles (4) soap - water mixing with 50 cycles then Neodol ® addition and mix 50 cycles (5) components mixed all at once i.e. no sequential mixing.

(6) In addition to the approx. 12% water content of the soap noodles used.

(7) See processing details below

Mixing all ingredients together without sequential mixing results in a formation of white soap and sequential mixing was preferably found to produce iridescence as discussed above. Although not wishing to be bound to the following theoretical explanation, it is speculated that since ethoxylated alcohols have a strong affinity towards water, the alcohols first interact with or are solvated by water and thus the water bound by the alcohols is not available for soap binding later in the process for making the soap bar. In order to ensure some soap solubilization, the mixing should be preferably conducted in at least two stages so that a maximum amount of water may preferentially bind to soap.

Sample Preparation Procedure for Examples 1 and 2:

The following procedure was used to prepare the toilet bars listed in tables 1A & B and 2 unless a different process variation is listed in the table for a given bar. Varying amounts of specific Neodol® alcohols specified in table 1 were added to a base blend having the following composition:

| | |
|---|---|
| Soap noodles | 88 g |
| Water | 5 g |

The soap noodles consisted of 85/15 Tallow/Palm Kernel Oil (PKO) and had a moisture content of about 12% (w/w)

Some formulations indicated in Table 2 also include other conventional soap additives such as glycerine. The formulas were processed in a lab intensive mixer illustrated in FIG. 13.

The intensive mixer further includes a stainless steel cylinder 14 having dimensions of 4.5 inches (11.4 cm) height and 5.5 inches (14 cm) in diameter containing a movable piston 16 with perforated plate 12. The perforations allow the soap 18 to pass through during plate movement. Rapid movement of the plate causes high shear to be exerted on the material during its passage through the holes 14 in the plate 12. Shear is quantified using Instron load cell 20.

Soap mixing was preferably conducted in two stages;

1) Soap noodles and water were mixed first (one time cycling at 50 mm/min then 24 cycles with speed of 500 mm/min) at a temperature of 23 C and
2) Neodol® alcohol was then added and mixed (1 time cycling at 50 mm/min and then 24 cycles at 500 mm/min) at a temperature of 23 C.

The product was next placed in a plastometer 10 (see FIG. 11) with dimensions 3.2 cm inside diameter×36 cm depth and with jacketed walls 12 for temperature control and having a solid plunger 14 for material 16 compression. The material 16 was compacted with an initial force of 6-10 kN and left for 30 min at 40 C to allow material relaxation. Following this, the plug of material 16 was pushed (extruded) out and cut into 1 cm strips (pellets) using a thin metal wire of 0.5 mm in diameter. The appearance of the pellets was analysed using the Hunter calorimeter according to the procedure described below. Two conventional sized soap bars were also stamped using longer strips of the soap plugs (diameter=1 cm).

EXAMPLE 3

Selected iridescent soap bars were characterized using a multiple angle spectrophotometer according to the procedure described below. It was observed that the color hue appears different depending on the viewing angle for the inventive bars. In order to quantify that effect, reflectance of selected soap bars were measured at different angles (15, 25, 45, 75 and 110 degrees) using a Portable Multi-Angle X-rite MA68 Spectrophotometer. For a comparative opaque whitish sample [i.e. sample 10A of table 1], the reflectance characteristics were found to be independent of the viewing angle (please see FIG. 4), i.e. the ratio of blue (440 nm) to green (570 nm) reflectance value is about 0.75 for all viewing angles measured.

FIG. 5 shows the same measurement conducted on iridescent soap sample 4A. It can be observed that there is a peak appearing in the blue region (approx. 420-440 nm) and an apparent reflectance decrease in the green region (approx. 500-570 nm) and an increase towards longer wavelengths (>570 nm). As the viewing angle increases, the ratio of reflectance intensity in the blue wavelength at 440 nm to reflectance intensity in yellow 570 nm decreases indicating that the blue color is more visible at the smaller viewing angles that were used.

To better evaluate reflectance as a function of viewing angle, it was of interest to compare the reflectance of a comparative non-iridescent translucent soap sample 7*x* (FIG. 6 and Table 3) with one of an inventive iridescent sample 4A. There is no peak visible within the blue region (FIG. 6). The reflectance ratio at 440/570 nm is decreased to 0.33. FIG. 8 shows reflectance spectra for several inventive iridescent translucent samples described in Tables IA or 2, along with two opaque samples i.e. inventive 9A and comparatives 10A from Table 2. Comparative sample 10A did not show any iridescence (i.e. b=9.7).

TABLE 3

Composition of sample 7X

| Ingredient name | wt % |
|---|---|
| lauric acid | 5.53 |
| myristic acid | 3.73 |
| palmitic acid | 15.58 |
| stearic acid | 16.47 |
| oleic acid | 21.45 |
| linoleic acid | 1.94 |
| linolenic acid | 0.08 |
| archidic acid | 0.03 |
| Sodium hydroxide | 9.42 |
| EHDP | 0.02 |
| EDTA | 0.05 |
| Sorbitol | 8.40 |
| PKOFA | 1.22 |
| PPG | 1.47 |
| TEA | 1.47 |
| NaCl | 0.05 |
| Water | 13.09 |

Preparation method: Anhydrous soap was prepared in M-20 Ploughsare Mixer (Littleford-Day, Florence, Ky.) equipped in four plough shape blades and two angled scraper blades and a chopper centrally located in the vessel. The soap was prepared by combining melted Tallow fat and palm Kernel Oil, heating the mixture to 95 C, adding a stoichiometric quantity of 50% aqueous sodium hydroxide to fully neutralize the fatty acids, removing the heat source and allowing it to react for 8 minutes (max temperature reached at that stage was 116 C). When the batch cooled to 105 C all components but palm kernel fatty acid were added and the mixing continued. At about 93 C Palm Kernel fatty acid was added to the batch and mixed for additional 50 minutes. When the mixing time approached 70 minutes, the batch was removed (at 80 C) and the material was milled three times at 23 C in Mazzoni 3 Roll Mill (Mazzoni L B, Bustro Arsizio-Italy). Following this the material was placed in Mazzoni M100 plodder and extruded seven times.

The effect of translucency (or conversely opacity) of samples 4A, 6A and 9A was assessed with respect to their reflectance curves and is depicted in FIG. 8. Sample 4A appears most translucent and thus the reflectance curve resembles most the curve obtained on the translucent soap sample (FIG. 7) with the exception that now there is a peak appearing in the blue region for 4A. Sample 6A appears more opaque than 4A but less than 9A. Its reflectance characteristics were found to fall between sample 4A and the opaque sample 9A.

EXAMPLE 4

The effect of background color on the observed appearance of two inventive Toilet bars was assessed according to the procedure described below and is summarized in Table 5 below. The two bars have the same composition (see sample B5 in Table 2) but were processed slightly differently where for bar A, the soap-water blend was mixed 1 cycle@50 mm/min, then Neodol® was added and then mixed 25 cycles@300 mm/min and for bar B the soap-water blend was mixed 50 cycles@300 mm/min, and after Neodol® addition it was processed as above. Sample B is more iridescent than sample A. It was found that a red color background accentuated the apparent iridescent blue hue compared to the other background colors tested.

TABLE 4

Iridescent soap bar appearance as a function of background color:

| Background Color | Bar A | Bar B |
|---|---|---|
| Red | + | +++ |
| Yellow | + | + |
| Blue | 0 | 0 |
| Green | 0 | + |
| Orange | 0 | + |
| Tan | 0 | + |

Notes:
0 means no detectable blue color appearance
\+ means slight blue color appearance
++ means moderate blue color appearance
+++ means strong blue color appearance Procedure:

Soap bar samples were placed on colored cardboard papers, cut out of Manilla folders obtained from Smead Paper Supply Co.

Colors are defined as follows:

Red UPC 10267 No H163R

Yellow UPC 10271 No H163Y

Blue UPC 10287 No H163SBE

Green UPC 10247 NO H163GN

Orange UPC 10259 No H163 R

Tan UPC 10333 No 153L-3

EXAMPLE 5

The b color value at different viewing angles for selected formulations in Table 5 below was measured and is depicted in FIG. 8. The blue color is the most intense at 45 degrees from specular angle (i.e. 90 degrees to the sample surface), and the yellow color is strongest when viewing the sample surface at 110 degrees from specular angle. The composition of the samples used for measurements are listed in Table 1A and Table 5.

TABLE 5

Soap samples obtained by shear intensive processing

| Sample | Neodol ® type alcohol | Neodol ® Concentration wt [%] | Ratio of alcohol conc. (wt. %) to eo number |
|---|---|---|---|
| 1a | 25-7 | 5.1 | 0.73 |
| 3a | 25-7 | 4.1 | 0.57 |
| 4a | 23-6.5 | 7 | 1.08 |
| 6a | 23-6.5 | 3.1 | 0.48 |
| 9a | 25-3 | 3.1 | 1.03 |
| 10a | 23-1 | 7 | 7 |

The process included mixing soap and water in the Intensive mixer for 1 cycle @50 mm/min, adding the listed Neodol® alcohol and mixing 25 cycles@500 mm/min. The mixture was then placed in the plastometer, compressed, relaxed (i.e. compression released for a specified time) and the soap material pushed out in the form of a small round billet. The billet was cut into 1 cm strips which were then used for b color measurements.

EXAMPLE 6

Selected inventive (3*a*: 87.8% soap & 4.1% alcohol, see Table 1A) and comparative (15-117-6: 90% soap & 4% alcohol, see Table 2) opaque soap bars having similar chemical compositions were prepared as described below.

Sample 15-117-6 was processed using conventional soap mixing equipment (3600 gms (90% by wt.) Anhydrous soap 85/15 was placed in Winkworth 10Z sigma-blade mixer, (Winkworth Machinery Ltd, Staines, England), 200 gms (5% by wt.) water was added and mixed at 23 C for 30 min at 1200 rpm. Then 160 gms (4% by wt.) Neodol 25-7 was added and the mixing continued for 1 hour and 20 minutes. The product was milled one time at 23 C in Mazzoni 3 Roll Mill. Following that the material was placed in Mazzoni M100 plodder and extruded. The inventive sample designated as 3A (see Table 1A) with the same chemical composition was processed using the lab intensive mixer described earlier (soap-water mixed at 23 C 12 cycles @300 mm/min and after Neodol 25-7 addition the sample was mixed at 23 C 25 cycles @300 mm/min). The sample was then placed in a plastometer, compressed to 5 kN and relaxed for 30 min. Following that it was extruded and cut into 1 cm strips The samples were analysed after ageing them for approximately 5 months in closed polyethylene bags stored in an air conditioned room (temp between 20 to 24 C under fluorescent lighting).

Small angle x-ray diffraction analysis according to the procedure described below was employed to investigate the presence or absence of any internal microstructural organization within the samples. The comparative sample showed some larger, disordered structure (scatter at lower angles), and the lamellar peaks appeared to be broader, perhaps indicating two lamellar structures with spacing of 40 and 42 angstroms. In the inventive sample, the lamellar peaks were seen to be much sharper with a layer thickness of 40 angstroms indicating more ordered structure.

EXAMPLE 7

The average work upon the addition of the Neodol® alcohol in the soap bar blends described in Table 6 was measured using an Instron Mechanical Tester Model 5569 (Instron, Norwood, Mass.). Neodol® type alcohol(s) is/are preferably added to the soap-water preblend as discussed above. In this preferred embodiment, the inventive iridescent soap blend is mixed in two parts; first the soap and water are mixed (first stage) and then followed by addition of the ethoxylated alcohol (second stage). The first stage of mixing is the same for all formulas illustrated in Table 6 since it refers to soap-water mixing. Although the measured force might vary due to water content, no significant variation is observed in the range of water concentrations used. The work necessary for the first and second stage mixing is measured using an Instron Mechanical Tester. The work for each cycle is recorded and then averaged to obtain the mean work value.

As discussed above, the second stage of mixing requires the addition of various Neodol® alcohols and the work required to mix them into the soap-water mass was seen to vary for several formulations and an example is plotted in FIG. 9 versus the number of ethoxyl-groups on the alcohol for two Neodol concentrations, i.e. 3% and 7% by weight. Various alcohol chain lengths were tested (see e.g. Table 6). The degree of alcohol ethoxylation was seen to affect mixing work more than the other variables. Comparative Neodol® 23-1 with the shortest carboxylate chain and with the least degree of ethoxylation shows the most effect on work reduction during the second stage of mixing indicating that one needs to input less work to produce iridescence in that soap material. However, in this case the blue hue iridescence is weak and variable. It is observed that overall the more Neodol® alcohol in the formula the larger the effect on work reduction. The most work was required for an alcohol mixture of C14 and C15 alkyl chain length with 7 ethoxyl groups. The Iridescent Work Index (IWI) is a defined parameter that further characterizes a preferred embodiment of the inventive iridescent soap bars. As discussed above, the IWI is defined as the product of ethoxylation number multiplied by the work (kJ) necessary to process the soap formula to obtain the iridescent effect. It was found that this index closely correlates with b values for various inventive formulations described in Table 6 below and plotted in FIG. 10.

TABLE 6

Iridescence work index ("IWI") for various Neodol ® alcohols

| Neodol type | work/ cycle [kJ] | conc [% by wt.] | Ethoxyl number | Ratio of alcohol conc. To EO number | b | Iridescence Work index - IWI (1) |
|---|---|---|---|---|---|---|
| 25-7 (Inv.) | 3.7 | 7 | 7 | 1.0 | −5.6 | 25.9 |
| 45-7 (Inv.) | 4.16 | 7 | 7 | 1.0 | −11.7 | 29.1 |
| 25-7 (Inv.) | 3.3 | 5.1 | 7 | 0.72 | −17.8 | 23.1 |
| 23-6 (Inv.) | 3.3 | 5.1 | 6.5 | 0.78 | −8.4 | 21.5 |
| 25-3 (Comp.) | 2.9 | 7 | 3 | 2.33 | 4.7 | 8.7 |
| 25-3 (Inv.) | 2.9 | 5.1 | 3 | 1.70 | −4.6 | 8.7 |
| 145-b-2 (Inv.) | 3.35 | 4 | 2 | 2.0 | −6.1 | 6.7 |
| 23-1 (Comp.) | 2.1 | 7 | 1 | 7.0 | 9.7 | 2.1 |
| 23-1 (Comp.) | 2.37 | 5 | 1 | 5.0 | 8.1 | 2.4 |

Note:
(1) eo number * work (KJ)

Iridescence was seen to increase with the decrease in b value and with increase of IWI (FIG. 10) for the two concentrations of Neodol® tested i.e. 5.1 and 7%.

TABLE 7

| Sample | Neodol ® Alcohol | Alcohol conc [%] | Avg Work/cycle (J) |
|---|---|---|---|
| 1 a 1 | 25-7 | 5 | 4545 |
| 2 a 1 | 25-7 | 2 | 4595 |
| 3 a 1 | 25-7 | 3 | 4254 |
| 4 a 1 | 23-6.5 | 15 | 4198 |
| 5 a 1 | 23-6.5 | 10 | 4166 |
| 6 a 1 | 23-6.5 | 2 | 4256 |
| 7 a 1 | 25-3 | 10 | 4450 |
| 8 a 1 | 25-3 | 4 | 4151 |
| 9 a 1 | 25-3 | 0 | 4271 |
| 10 a 1 | 23-1 | 9 | 4100 |
| 11 a 1 | 23-1 | 1 | 4143 |
| 12 a 1 | 23-1 | 0 | 4125 |
| 13 a 1 | 45-7 | 4 | 4867 |
| 14 a 1 | 45-7 | 8 | 4785 |
| 15 a 1 | 45-7 | 4 | 4534 |

88% soap, 5% water, Neodol as indicated

TABLE 8

| Sample | Neodol ® Alcohol | Alcohol conc [%] | Avg Work/cycle (J) |
|---|---|---|---|
| 2 a 11 | 25-7 | 7 | 3688 |
| 1 a 11 | 25-7 | 5 | 3508 |
| 3 a 11 | 25-7 | 4 | 3342 |
| 4 a 11 | 23-6.5 | 7 | 3285 |
| 5 a 11 | 23-6.5 | 5 | 3280 |
| 6 a 11 | 23-6.5 | 3 | 3582 |
| 7 a 11 | 25-3 | 7 | 2898 |
| 8 a 11 | 25-3 | 5 | 2880 |
| 9 a 11 | 25-3 | 3 | 3460 |
| 10 a 11 | 23-1 | 7 | 2075 |
| 11 a 11 | 23-1 | 5 | 2371 |
| 12 a 11 | 23-1 | 3 | 2932 |
| 13 a 11 | 45-7 | 7 | 3949 |
| 14 a 11 | 45-7 | 5 | 4159 |
| 15 a 11 | 45-7 | 3 | 4021 |
| 16 a 11 | 145b-2 | 7 | 2797 |
| 17 a 11 | 145b-2 | 5 | 3362 |
| 18 a 11 | 145b-2 | 3 | 3330 |

88% soap, 5% water, Neodol as indicated

Soap and water mixes readily in the intensive mixer. It was found that 1 mixing cycle in the first stage (i.e. soap and water), when followed by 25 mixing cycles in the second stage (i.e. with Neodol® alcohol addition), was sufficient to impart iridescence for the inventive bars. The effect of the number of cycles (in the range of 10 to 40 total cycles) in the second stage on b value was determined after addition of ethoxylated alcohol. The results showed that after 10 cycles, the b value was −2 and after 20 and 30 cycles it was −6 while for 40 cycles it was −7. While not wishing to be bound by the following theoretical discussion, this finding supports that the more work generated for ethoxylated alcohol mixing, the more ordered structuring apparently occurs within the soap and thus soap bar iridescence becomes more intense.

Further work was undertaken to evaluate the effect of shear on similar soap compositions. Referring to Example 6, sample 15-117-6 [(Table 2) having a similar composition to sample 3*a* in Table 1A, (containing Neodol 25-7 added after the water-soap blending)], was processed with comparatively low shear equipment (i.e. a Winkworth 10Z Mixer (4KG) then milled followed by extrusion and the resulting product did not show iridescence. For comparison sample 15-117-20 [(Table 2) containing 88% soap, 5% water and 7% Neodol® 25-9] was also processed under low shear conditions and no iridescence was detected. In this case the soap noodles were milled twice using a Mazzoni 3 Roll Mill, then water was added and mixed 30 minutes at 23 C. Neodol 25-9 was added and mixed for 45 min at 23 C, milled two times using the 3 Roll Mill, extruded using a Sigma Mini Plodder SB-18 (Sigma Engineering, White Plains, N.Y.) and then stamped using a Sigma SB-14 Press Bar. However, some iridescence was detected when a billet of this material was additionally exposed to high shear forces via extrusion from the plastometer. In this case a "b" value of −0.8 was measured indicating sufficient ordered structure to impart detectable iridescence to the soap sample.

While not wishing to be bound by the following theoretical discussion, the Winkworth 10Z mixer employed in the above example apparently does not provide enough of the extensional work required to produce measurable iridescence due to its inability to created the ordered layered structure required for iridescence. The effect of additional processing conducted on Mazzoni 3 Roll Mill (i.e. which provides some additional extensional shear) imparted no noticeable improvement upon iridescence intensity after additional milling. The b value for the final product was determined to be 3, 6 and 5.5 after 1, 2 and 5 repetitive milling tests respectively.

Test Methods:

Sample Appearance Measurement (L, a, b, Reflectance and Opacity):

A Hunter LabScan XE full scanning spectrophotometer with a wavelength range from 400 to 700 nm was used (Hunter Associates Laboratory, Reston, Va.). The sample was illuminated by a xenon flash lamp and reflected light is collected by a 15-station fiber optic ring. All measurements were conducted with specular reflectance excluded. Color values, L brightness, a-redness and b-blue, reflectance or opacity which is a ratio of reflectance values against white and against black background, were measured.

To measure color values or reflectance characteristics, the sample is measured three times using a white ceramic plate as a background. For opacity measurements, the sample is placed at a port and covered with a white plate. Three readings are taken. The sample is then covered with black ceramic plate and measured again (average of 3). After turning the sample to the other side, the measurement is repeated and the result is averaged.

Additional spectral reflectance measurements were made with an X-Rite MA-68 multi-angle spectrophotometer (X-rite, Inc, Grandville, Mich.) at various viewing angles. Blue-enhanced silicone photodiodes act as light receivers. This instrument illuminates the sample at 45° from the sample plane with a gas-filled tungsten lamp, (color corrected to approx. 4000° K.) and measurements are taken at 15, 25, 45, 75 and 110° from the specular angle. The instrument was calibrated using X-Rite calibration references. In order to avoid the introduction of scratch artefacts from the samples, a measurement jig was fashioned to only allow the measurement area of the X-Rite instrument to be in contact with the sample. All measurements were made at room temperature (approximately 23 C). Five measurements were conducted on each sample with the closest three averaged to reduce any sample anomalies. Spectral reflectance (at 10 nm intervals), CIE L*, a*, b*, C* (Chroma) and h* (hue angle) at each of the angles (15, 25, 45, 75 and 110°) were measured.

Small Angle X-Ray Diffraction:

Small angle x-ray diffraction measurements were conducted with an Anton Paar SAXSess, (Anton Paar, Ashland Va.) which is an X-ray instrument capable of simultaneous wide and small angle scattering (SWAXS). The instrument is aligned in a line focus/line collimation configuration. An incident beam multilayer parabolic mirror is used to increase the primary beam flux and to provide a monochromic beam. The X-rays are produced by a Panalytical 2.2 kW sealed Cu X-ray source. Power is supplied to the tube by a Panalytical PW3830 X-ray generator set at 40 kV and 50 mA.

The solid soap sample was prepared by cutting a thin slice from the bulk material using a new, clean razor blade. This thin slice was then placed between two windowed copper plates in a SAXSess sandwich holder.

The sandwich holder with sample is loaded into the instrument sample stage. The stage has previously been aligned to ensure proper positioning of the sample in the primary beam.

A SWAXS image plate is loaded into the camera for data collection. The dimensions of this image plate are 200 mm×60 mm, allowing for a scattering angle collection range from 0°-45° in 2θ.

The instrument housing is evacuated using a standard rotary roughing pump.

The sample is exposed to the primary beam for 4 minutes.

After the exposure is complete, the lights in the room are turned off (the image plate will be erased slowly by light) and the image plate is transferred into the Perkin-Elmer image plate reader (Model B431201, Perkin-Elmer Company, Waltham, Mass.).

The image data is converted to a tiff file in Optiquant (software) and saved to the hard drive.

The tiff file is then opened in SAXSquant (software) for data reduction according to the following protocol:

1) Define primary beam end points
2) Define integration region (10 mm wide strip along length of image plate, shown in red in the images contained in the report)
3) 'Normalize' integration region. This makes the integration region perpendicular to the primary beam and centered on the primary beam.
4) Integrate the intensity->this generates an intensity vs. distance profile
5) In this profile, define the origin (primary beam) location.
6) Convert to q vs. Intensity
7) Save data Convert to 2θ vs. Intensity in Excel® spreadsheet Method for Calculation of Yield Stress with Cheese Cutter Device An approximate value for yield stress can be determined by the cheese cutter method. The principle of the measurement is that a wire penetrating into a material with a constant force will come to rest when the force on the wire due to stress balances the weight. The force balance is:

Weight driving wire=force on wire due to material stress $$mg=KyslD$$

where m=mass driving wire (actual mass used in calculation is the mass placed on the device plus the weight of the arm which adds to the extra weight on the sample)

g=gravitational constant, 9.8 m/sec$^2$ ys=yield stress l=length of penetration of wire into soap after 1 minute (mm)

D=diameter of wire (mm)

K=a geometrical constant

The final equation is:

$$ys=(3/8)m\,g/(lD)$$

Procedure:

Cut a square of toilet bar and position on the yield stress device. Place a mass on the yield stress device while holding the arm. 400 g is an appropriate mass, although less might be needed for a very soft material. Gently lower the arm so the wire just touches the bar sample and let the arm go. Stop the vertical motion of the arm after one minute, and push the soap through the wire horizontally to cut a wedge out of the sample. Take the mass off the device and then measure the length of the cut in the sample. The wire would continue to cut the sample at a slow rate, but the length of the cut made by the wire in one minute is taken as the final value. Measure the temperature of the sample while the test proceeds.

Sample Calculation:

A 400 gram weight is used on the yield stress device and a 22 mm slice is measured where the wire has cut the sample after 1 minute. Assuming the diameter of the wire is 0.6 mm, the approximate yield stress is $$\frac{(3/8)(400+56)[\text{g}]\,9.8\,[\text{m/sec}^2]\,10^{-3}[\text{kg/g}]}{22[\text{mm}]\,0.6\,[\text{mm}]\,10^{-6}[\text{m}^2/\text{mm}^2]} = 1.3105\,Pa \text{ or } 130\,kPa$$

Optionally an Instron testing device (supplied by Instron Co., Boston, Mass.) may be used instead of a weight to apply stress to the wire contacting the solid cleansing phase mass.

The foregoing description and examples illustrate selected embodiments of the present invention. In light thereof variations and modifications will be suggested to one skilled in the art, all of which are within the scope and spirit of this invention.

We claim:

1. A toilet bar comprising:

a. an iridescent continuous phase and an ordered, layered microstructure;

b. at least 10% by wt. of a soap;

c. about 0.1 to about 20% by wt. of total C8 to C24 ethoxylated alcohol(s) with a ratio of methylene number to ethoxyl number in the range of 12 to 1.2;

d. wherein the ratio of ethoxylated alcohol(s) concentration to ethoxyl number is less than 2.3;

e. wherein the ratio of total bound water in the toilet bar to water bound to the soap is greater than 1.0 and (f) wherein said soap bar produces a blue iridescence characterized by a b* measurement of −1 or less using the standard L a b Color Space method.

2. The toilet bar of claim 1 wherein the bar contains one or more C11 to C15 ethoxylated alcohol(s) having between 2 to 10 moles of ethoxylation.

3. The toilet bar of claim 2 wherein the ethoxylated alcohols are present in the concentration range of about 0.1 to 9% by wt.

4. The toilet bar of claim 1 wherein the bar has a yield stress value from about 15 Kpa to 800 KPa at 25° C. and 50% RH.

5. The toilet bar of claim 1 wherein the bar has been processed with a quantity of work of mixing equivalent to an Iridescence Work Index of at least 5.

6. The toilet bar of claim 1 wherein the bar contains about 40 to about 85% by wt. of a C6 to C22 fatty acid soaps.

7. The toilet bar of claim 1 further comprising about 3 to 22% by wt. of total water.

8. The soap bar of claim 1 further comprising 0 to about 20% by wt. of a synthetic anionic surfactant.

9. The soap bar of claim 8 wherein the synthetic anionic surfactant is selected from C8 to C14 acyl isethionates; C8 to C14 alkyl sulfates, C8 to C14 alkyl sulfosuccinates, C8 to C14 alkyl sulfonates; C8 to C14 fatty acid ester sulfonates, derivatives, and blends thereof.

10. A process for making iridescent soap bar of claim 1 comprising the steps of:

a. mixing fatty acid soap(s) with sufficient water to saturate all soap sites capable of complexing water until a uniform preblend is obtained;

b. adding the ethoxylated alcohol(s) to the uniform preblend formed in step (a);

c. mixing the product of step (b) in a high shear processor under conditions sufficient to impart a work level effective to produce an iridescent high shear blended product;

d. ejecting the blended product from the processor; and e. forming the ejected blended product into shaped soap bars.

11. The process of claim 10 where the quantity of work level is equivalent to an Iridescence Work Index of at least 5.

12. The method of claim 10 where the preblend is further processed with a high extension shear mixer.

13. The method of claim 10 where the ejected blended product is additionally compressed, and extruded then stamped or extruded then cut to obtain shaped soap bars.

* * * * *